US008974580B2

(12) United States Patent
Wang

(10) Patent No.: US 8,974,580 B2
(45) Date of Patent: Mar. 10, 2015

(54) MODIFICATION OF COLD JET NOZZLE IN A JET MODULATOR DESIGN FOR COMPREHENSIVE TWO-DIMENSIONAL GAS CHROMATOGRAPHY

(71) Applicant: ExxonMobil Research and Engineering Company, Annandale, NJ (US)

(72) Inventor: Frank C. Wang, Annandale, NJ (US)

(73) Assignee: ExxonMobil Research and Engineering Company, Annandale, NJ (US)

(*) Notice: Subject to any disclaimer, the term of this patent is extended or adjusted under 35 U.S.C. 154(b) by 148 days.

(21) Appl. No.: 13/733,223

(22) Filed: Jan. 3, 2013

(65) Prior Publication Data

US 2013/0174738 A1 Jul. 11, 2013

Related U.S. Application Data

(60) Provisional application No. 61/584,449, filed on Jan. 9, 2012.

(51) Int. Cl.
| B01D 53/02 | (2006.01) |
| B01D 53/04 | (2006.01) |
| G01N 30/46 | (2006.01) |
| G01N 30/30 | (2006.01) |
| G01N 30/12 | (2006.01) |

(52) U.S. Cl.
CPC .... B01D 53/0438 (2013.01); *G01N 2030/3023* (2013.01); *G01N 2030/122* (2013.01); G01N 30/463 (2013.01); G01N 30/465 (2013.01)
USPC .................. 96/101; 96/104; 95/87; 73/23.41

(58) Field of Classification Search
CPC .............. G01N 30/463; G01N 30/465; G01N 2030/3015; G01N 2030/121; G01N 2030/122; B01D 53/0438
USPC .............. 96/101, 104; 95/87; 73/23.35, 23.42
See application file for complete search history.

(56) References Cited

U.S. PATENT DOCUMENTS

| 6,007,602 A * | 12/1999 | Ledford et al. ...................... 95/8 |
| 6,190,613 B1 * | 2/2001 | Watanabe et al. ............. 422/500 |
| 6,547,852 B2 * | 4/2003 | Ledford et al. .................... 95/87 |
| 6,838,288 B2 * | 1/2005 | Beens ........................... 436/161 |
| 7,258,726 B2 | 8/2007 | Ledford, Jr. |
| 7,306,656 B2 * | 12/2007 | Lange et al. .................... 96/101 |
| 7,490,506 B2 * | 2/2009 | Chaintreau et al. ........... 73/23.41 |
| 8,277,544 B2 * | 10/2012 | Guan et al. ....................... 96/101 |
| 2005/0106743 A1 * | 5/2005 | Zilioli et al. .................... 436/161 |

FOREIGN PATENT DOCUMENTS

WO 0239106 A1 5/2002

OTHER PUBLICATIONS

PCT Search Report issued in corresponding PCT Application No. PCT/US2013/020187 dated Apr. 11, 2013 (4 pp).
PCT Written Opinion issued in corresponding PCT Application No. PCT/US2013/020187 dated Apr. 11, 2013 (6 pp).

* cited by examiner

*Primary Examiner* — Robert Clemente
(74) *Attorney, Agent, or Firm* — Glenn T. Barrett; Andrew T. Ward

(57) ABSTRACT

A collimator fixed to the cold jet nozzle of a modulator of a two-dimensional gas chromatograph to aid in the alignment of the cold jet nozzle and loop modulator tube.

16 Claims, 4 Drawing Sheets

MODIFICATION OF COLD JET NOZZLE IN A JET MODULATOR DESIGN FOR COMPREHENSIVE TWO-DIMENSIONAL GAS CHROMATOGRAPHY

FIELD OF THE INVENTION

The presently disclosed subject matter relates to improvements to two-dimensional gas chromatography (GC×GC). In particular, the presently disclosed subject matter relates to an improvement of the modulation of the system.

BACKGROUND OF THE INVENTION

A hot jet, cold jet and a loop modulation system in a two-dimensional gas chromatograph are disclosed in U.S. Pat. No. 7,258,726 to Ledford. Ledford discloses a modulation tube having a loop modulator structure. Two portions of the modulation tube can be thermally modulated simultaneously by a thermal modulation device which includes a cold jet assembly including a cold jet nozzle, and a hot jet assembly including a hot jet nozzle to modulate the temperature of portions of the modulation tube. This modulation system, which requires one set (cold and hot) jets to achieve the modulation process is an improved design from an older dual-Jet modulation system.

The loop modulator employs hot and cold jets of gas to effect two-stage thermal modulation. The two stages are formed by looping a segment of capillary tubing through the path of a single cold jet. The tubing between the two cold spots thus formed comprises a delay loop. An example of the mechanical assembly of the loop modulator is illustrated in FIG. 1. The cold jet subassembly 1 consists of a steel tube of approximately 3.0 mm inside diameter housed in a steel outer tube of some 19 mm outside diameter. The space between the inner and outer tubes is evacuated with a mechanical roughing pump and valved off, thereby forming a vacuum insulated housing around the cold jet. Vacuum insulation is essential for the introduction to the GC oven of a cryogenically cooled gas stream. A hot jet subassembly 2 is mounted at right angles to the cold jet by means of machined brackets, which also provide means of holding the modulator tube in the paths of the gas jets. The loop modulator tube 3 is housed in a folded metal holder 4 studded with machined "buttons" which mount in slots milled into the bracket structure. The loop modulator tube is held in place within the modulator holder by a folded piece of Kapton (Dupont) film 5, which functions as a spring tensioner. The modulator tube is installed and uninstalled in a matter of seconds by sliding it into or out of the slotted bracket structure 4.

In order for this loop modulator to work in the most efficient mode, it is required that the cold jet 1, hot jet 2 and the loop modulator tube 3 be aligned in a single point. At that specific point, the cold jet has the most cooling power to trap eluate through the looped modulator tube and the hot jet is the best focused to blow hot gas to release the trapped material in the looped modulator tube. The alignment scheme is shown in FIG. 1.

Since the cold jet subassembly consists of a steel tube of approximately 3.0 mm inside diameter, cold jet flow through the tube will further spread out due to free expansion when it passes into the open space below the cold jet. The length/area of column being cooled by this cold jet is slightly longer/larger than 3.0 mm with an uneven cooling efficiency through the entire cooled modulator tube covered by this cold jet. In the center of the cold jet, the column temperature will be the lowest and the modulator tube temperature will be higher at the edge of the cold jet coverage. The bottom view of the modulation tube is shown in the FIG. 2. The bottom view shows the loop modulator tube 3, cold jet 1, and hot jet 2.

This uneven modulator tube temperature and the length of the modulator tube being cooled by the cold jet will directly affect the trapping efficiency during the modulation in a comprehensive two-dimensional gas chromatography procedure. If there is a slight misalignment or the alignment has been changed during the experiment, the cold jet trapping process will become imperfect. However, the most significant impact on this imperfect trapping efficiency is the hot jet release process. In most cases, the hot jet either does not have enough thermal energy to completely release the eluent being trapped or does not spread wide enough to cover the entire length cooled by the cold jet. This will create a cold spot in the looped component that will cause the modulation operation to completely fail or cause every separated component to carry a long tail in the second dimensional separation. Both cold spots and tailing peaks will cause the failure of the comprehensive two-dimensional gas chromatography separation. However, the prior art modulator requires that the cold jet nozzle, hot jet nozzle, and loop modulator be properly aligned in order to reach the best efficiency of the modulation. Three point or three dimensional alignment of the hot jet, cold jet and modulation tube are required. If there is any one component misaligned, there will be a very significant impact on the modulation process and result in a failure of the comprehensive two-dimensional separation and any experimental results obtained therefrom.

There is a need for an improved modulator design for a comprehensive two-dimensional gas chromatography having improved alignment capabilities to enhance reliability.

SUMMARY OF PRESENT INVENTION

The presently disclosed subject matter is directed to a modification of the cold jet nozzle to make alignment simpler. A collimator is fixed to the end of the jet tube to allow alignment to be more easily achieved. The collimator includes a horizontal slot at its bottom end.

The presently disclosed subject matter is directed to an improved loop modulator system for a comprehensive two-dimensional gas chromatograph. The loop modulator system includes a cold gas jet assembly having a cold jet nozzle, a hot jet assembly having a hot jet nozzle, and a looped column of a modulator tube. The cold gas jet assembly directs a flow of cold gas from the cold jet nozzle towards the looped column. The hot jet assembly directs a flow of hot gas from the hot jet nozzle towards the looped column. The improvement to the loop modulator system includes a collimator connected to the cold gas jet assembly for modifying the flow of cold gas from the cold jet nozzle to produce a modified flow of cold gas. The collimator is preferably a tubular member having an opening at one end for securing the collimator to the cold gas jet assembly and an opening at an opposite end for modifying the flow of cold fluid from the cold jet nozzle. The opening for modifying the flow of cold gas is an elongated opening, whereby the modified flow of cold gas has a reduced cross-section area. The elongated opening is a rectangular opening. The collimator is preferably secured to the cold jet nozzle of the cold gas jet assembly.

The looped column and the cold jet nozzle are aligned such that a portion of the looped column intersects the modified flow of cold gas from the cold jet nozzle. The hot jet nozzle and the cold jet nozzle are aligned such that the flow of hot gas intersects the modified flow of cold gas from the cold jet nozzle. The hot jet nozzle and the looped column are aligned such that flow of hot gas intersects a portion of the looped column.

The presently disclosed subject matter is also directed to a comprehensive two-dimensional gas chromatography system having the improved loop modulator system.

DESCRIPTION OF THE PREFERRED EMBODIMENT

The presently disclosed subject matter is an enhancement of the cold jet nozzle to improve the modulation operation in a Jet-based modulation system for Comprehensive Two-Dimensional Gas Chromatography. The advantages of this modification for the cold jet nozzle (especially in a jet-based loop modulation design) includes: convert from a three-dimensional alignment to a two-dimensional alignment; improve the efficiency of the cold jet cooling, reduce costly coolant usage; and improve the hot jet releasing efficiency, easier for hot jet set-up.

In order to avoid those effects described above in connection with the prior art devices, a careful alignment among the cold jet, hot jet and the looped modulator tube is necessary before the comprehensive two-dimensional gas chromatography procedure. However, the temperature variation during the experiment will make this fragile alignment hard to maintain. The temperature variation of the modulation unit is significant because of the nature of the gas chromatography experiment; it can be varied from 40° C. to 390° C. It is hard to keep this three-dimensional alignment because of uneven thermal expansion of the modulation assembly during the temperature change. It will always result in imperfect modulation and may cause the failure of the comprehensive two-dimensional gas chromatography separation during the experiment.

Figure 1:
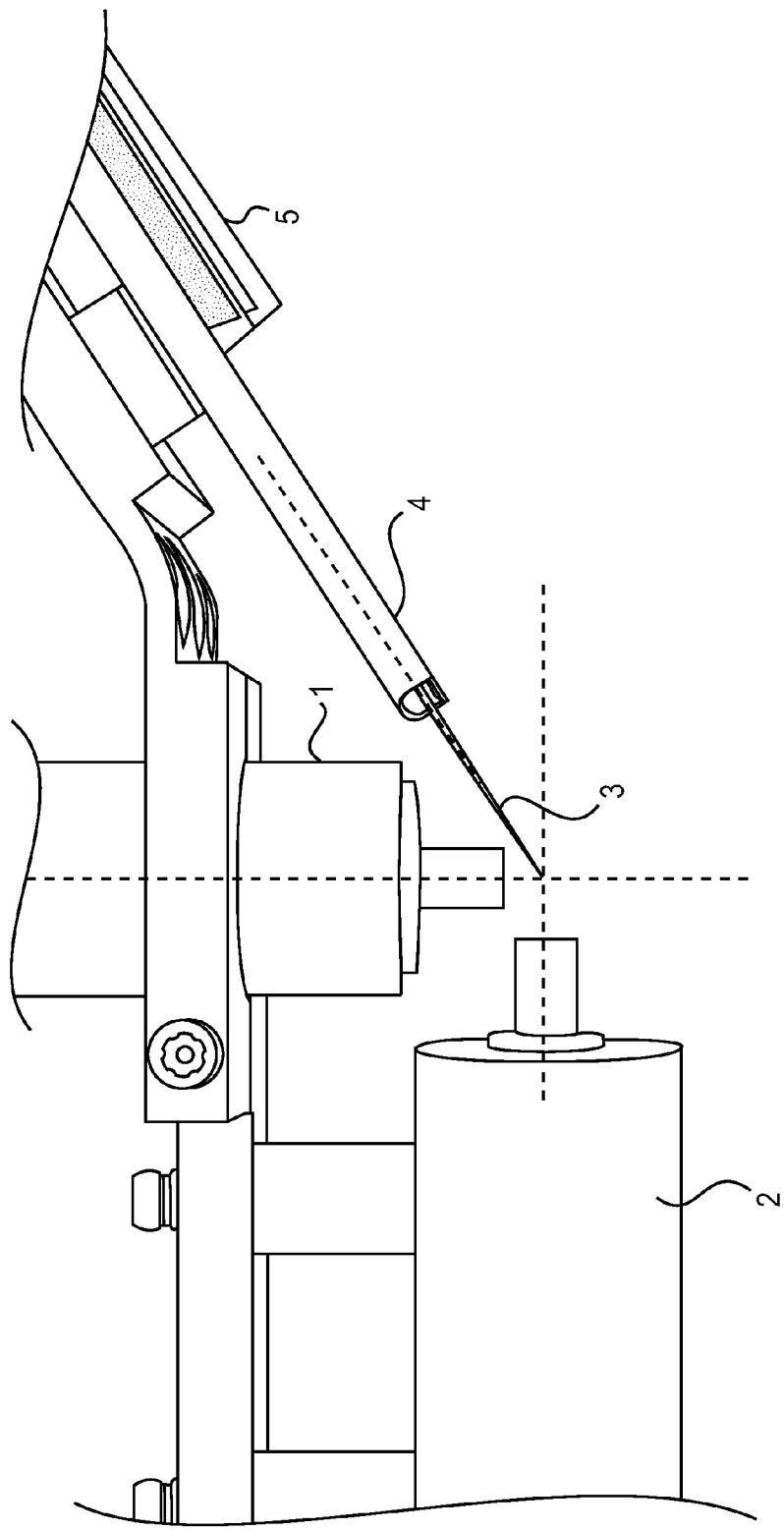
FIG. 1 is a schematic view of a thermal modulator having hot jet nozzle, a cold jet nozzle, and modulator tube according to the prior art.
Figure 2:
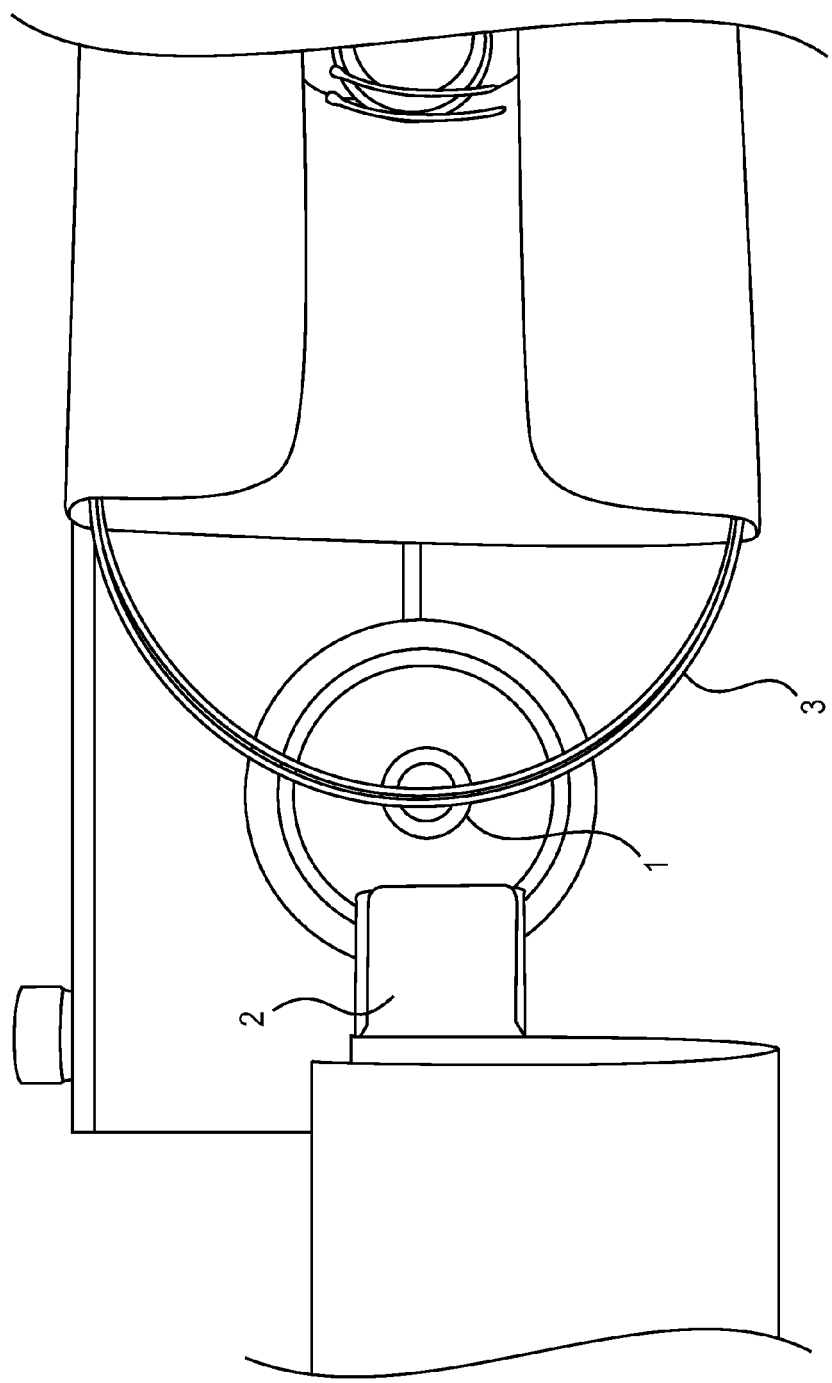
FIG. 2 is a bottom view of the thermal modulator of FIG. 1 from below the cold jet nozzle, hot jet nozzle and modulation tube.
Figure 3:
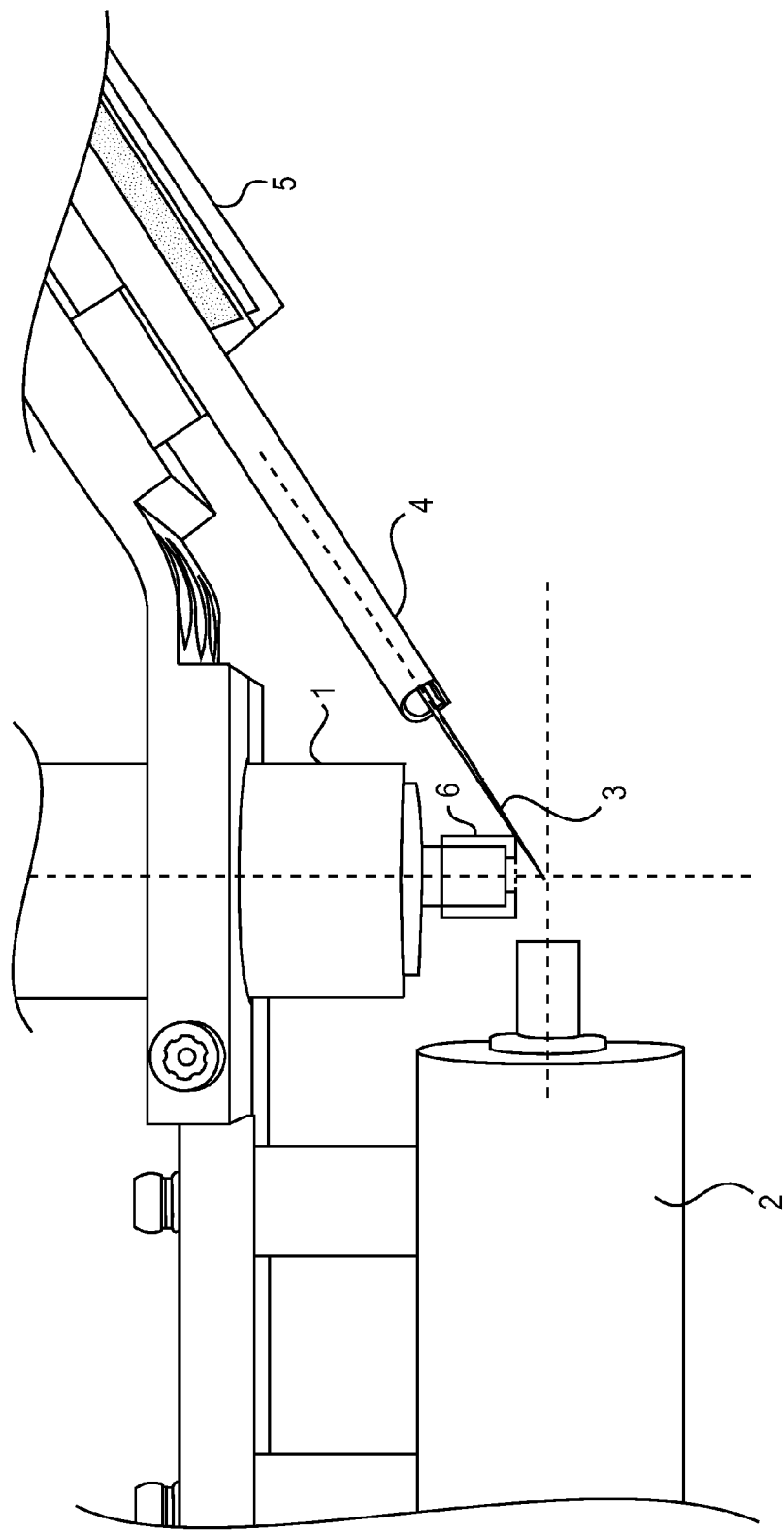
FIG. 3 is a schematic view of a thermal modulator in accordance with the presently disclosed subject matter.
Figure 4:
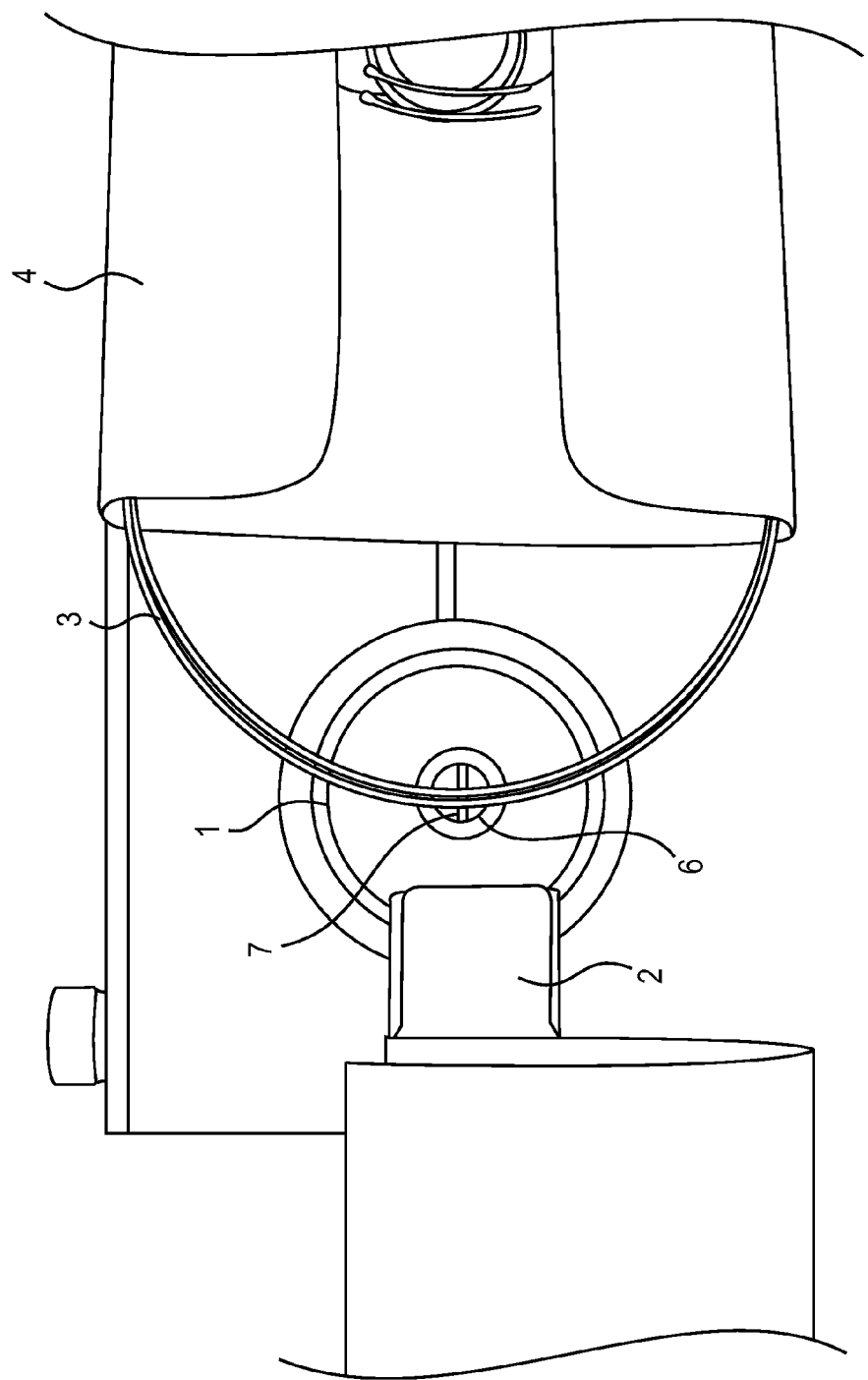
FIG. 4 is a bottom view of the thermal modulator of FIG. 3 in accordance with the presently disclosed subject matter from below the cold jet nozzle, hot jet nozzle and modulation tube loop with the collimator fixed to the cold jet.

It is necessary to improve the reliability and the efficiency of this loop modulation system. An improved thermal modulator system in accordance with the presently disclosed subject matter is shown in FIGS. 3 and 4. The thermal modulator system in accordance with the presently disclosed subject matter includes a cold jet subassembly 1. A hot jet subassembly 2 is mounted at right angles to the cold jet assembly 1. A loop modulator tube 3 is housed in a folded metal holder 4. The loop modulator tube is held in place within the modulator holder by a folded piece of Kapton (Dupont) film 5. The improved modulator system includes a collimator 6 connected to the output nozzle of the cold jet subassembly 1. The collimator 6 modifies the cold jet flow to increase the flexibility of this three-dimensional alignment requirement. FIG. 3 shows the collimator 6 fixed to the end of the cold jet nozzle 1. The collimator 6 is a tubular member having one open end that is secured to the end of the cold jet nozzle. The opposite end of the collimator 6 has an elongated opening 7 formed therein, as illustrated in FIG. 4. The elongated opening 7 is preferably a horizontally extending opening that is aligned with the hot jet nozzle.

The function of this collimator 6 is to reduce the size and shape of cold jet flow. The elongated opening 7 restricts the cold jet output flow from a 3.0 mm round shape to a 1.0 mm×3.0 mm rectangle shape. The presently disclosed subject matter is not intended to be limited to a 1.0 mm×3.0 mm rectangular shape; rather, other dimensions (both larger and smaller) are contemplated, provided such dimensions act to reduce the size and shape of the cold jet flow. Other shapes are also contemplated, provided such shapes act to reduce the size and shape of the cold jet flow in the above prescribed manner. There are numerous advantages to the use of the collimator 6 to the alignment of the components including: (i) a reduction in the cold jet effecting area, which makes the hot jet release process more complete and efficient; (ii) increasing the flexibility of cold jet alignment from one-point to a distance within about 3.0 mm, which effectively converts the three-dimensional alignment requirement between the three primary components (e.g., the cold jet subassembly 1, the hot jet subassembly 2 and the loop modulator tube 5) to a two-dimensional alignment requirement between only two of the three primary components (e.g., the hot jet subassembly 2 and the loop modulator tube 5); and (iii) decreasing the effect of temperature on the alignment of the components.

As illustrated in FIG. 4, the collimator 6 is fixed to the cold jet subassembly 1. The hot jet covers the area of the looped modulator tube that is cooled by the cold jet. In addition, the looped modulator tube can be placed within the 3.0 mm distance from the cold jet without changing the area of the looped modulator tube being cooled.

The collimated/modified cold jet assembly creates a new alignment procedure that is simpler and much more flexible than the original prior art design. In this modified version, the looped modulator tube needs only to be aligned with the hot jet. The hot jet needs to be focused on and blow through the modulator tube. The hot jet and modulator tube need to be aligned only within the 3.0 mm region that the collimated cold jet will flow through. Because of the rectangle shape of the cold jet collimator opening, any position within that 3.0 mm region of the cold jet flow area has the same cooling efficiency. This 3.0 mm region also provides the flexibility of the alignment among the hot jet, modulator tube, and cold jet.

Even with the temperature variation during the experiment, as long as the looped modulator tube remains within the hot jet blowing path and the looped modulator tube stays within the 3.0 mm region of the cold jet blowing path, the modulation system will work with the same efficiency and the comprehensive two-dimensional gas chromatography separation will succeed.

What is claimed is:

1. An improved loop modulator system for a comprehensive two-dimensional gas chromatograph, wherein the loop modulator system includes a cold gas jet assembly having a cold jet nozzle, a hot jet assembly having a hot jet nozzle, and a looped column of a modulator tube, wherein the cold gas jet assembly directs a flow of cold gas from the cold jet nozzle towards the looped column, wherein the hot jet assembly directs a flow of hot gas from the hot jet nozzle towards the looped column, the improvement comprising:
a collimator connected to the cold gas jet assembly for modifying the flow of cold gas from the cold jet nozzle to produce a modified flow of cold gas, wherein said collimator has at an opening at one end for securing the collimator to the cold gas jet assembly and an opening at an opposite end for modifying the flow of cold gas from the cold jet nozzle, wherein the looped column intersects the modified flow of cold gas, wherein the opening for modifying the flow of cold gas from the cold jet nozzle is oriented such that the modified flow of cold gas has a reduced cross-sectional area intersecting the looped column of the modulator tube.

2. The improved loop modulator system of claim 1, wherein the collimator is secured to the cold jet nozzle of the cold gas jet assembly.

3. The improved loop modulator system of claim 1, wherein the flow of hot gas intersects the modified flow of cold gas.

4. The improved loop modulator system of claim 3, wherein the flow of hot gas intersects a portion of the looped column.

5. The improved loop modulator system of claim 1, wherein the opening for modifying the flow of cold gas is an elongated opening.

6. The improved loop modulator system of claim 5, wherein the elongated opening is a rectangular opening.

7. The improved loop modulator system of claim 6, wherein the flow of hot gas intersects the modified flow of cold gas.

8. The improved loop modulator system of claim 7, wherein the flow of hot gas intersects a portion of the looped column.

9. A comprehensive two-dimensional gas chromatography system comprising:
   a loop modulator system, wherein the loop modulator system comprises:
   a cold gas jet assembly having a cold jet nozzle;
   a hot gas jet assembly having a hot jet nozzle;
   a looped column of a modulator tube, wherein the cold gas jet assembly directs a flow of cold gas from the cold jet nozzle towards the looped column, wherein the hot jet assembly directs a flow of hot gas from the hot jet nozzle towards the looped column; and
   a collimator connected to the cold gas jet assembly for modifying the flow of cold gas from the cold jet nozzle to produce a modified flow of cold gas; wherein said collimator has an opening at one end for securing the collimator to the cold gas jet assembly and an opening at an opposite end for modifying the flow of cold gas from the cold jet nozzle, wherein the looped column intersects the modified flow of cold gas, wherein the opening for modifying the flow of cold gas from the cold jet nozzle is oriented such that the modified flow of cold gas has a reduced cross-sectional area intersecting the looped column of the modulator tube.

10. The system of claim 9, wherein the collimator is secured to the cold jet nozzle of the cold gas jet assembly.

11. The system of claim 9, wherein the flow of hot gas intersects the modified flow of cold gas.

12. The system of claim 11, wherein the flow of hot gas intersects a portion of the looped column.

13. The system of claim 9, wherein the opening for modifying the flow of cold gas is an elongated opening.

14. The system of claim 13, wherein the elongated opening is a rectangular opening.

15. The system of claim 13, wherein the flow of hot gas intersects the modified flow of cold gas.

16. The system of claim 15, wherein the flow of hot gas intersects a portion of the looped column.

* * * * *